Figure 1:
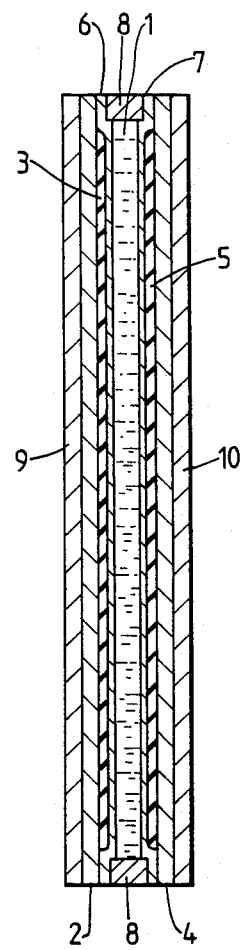

United States Patent [19]

Raynes et al.

[11] Patent Number: 4,753,752

[45] Date of Patent: Jun. 28, 1988

[54] SECONDARY ALCOHOL DERIVATIVES FOR USE IN LIQUID CRYSTAL MATERIALS AND DEVICES

[75] Inventors: Edward P. Raynes, Worcester; Ian C. Sage; John S. Lewis, both of Dorset, all of England

[73] Assignee: The Secretary of State for Defence in Her Britannic Majesty's Government of the United Kingdom of Great Britain and Northern Ireland, London, England

[21] Appl. No.: 897,159

[22] Filed: Aug. 18, 1986

[30] Foreign Application Priority Data

Aug. 19, 1985 [GB] United Kingdom ............... 8520715

[51] Int. Cl.$^4$ .................... G02F 1/10; C09K 19/12
[52] U.S. Cl. ................... 252/299.65; 252/299.01; 252/299.6; 252/299.5; 252/299.61; 252/299.62; 252/299.63; 252/299.64; 252/299.66; 252/299.67; 252/299.68; 350/350 S
[58] Field of Search ........... 252/299.6, 299.61, 299.62, 252/299.63, 299.64, 299.65, 299.66, 299.67, 299.68; 350/350 S; 560/59, 67, 72, 73, 55, 75, 102, 106, 107, 108, 109, 76, 118, 126, 8, 1; 544/318, 335; 549/372, 374, 375

[56] References Cited

U.S. PATENT DOCUMENTS

| | | | |
|---|---|---|---|
| 4,229,315 | 10/1980 | Krause et al. | 252/299.63 |
| 4,410,445 | 10/1983 | Baur et al. | 252/299.63 |
| 4,576,732 | 3/1986 | Isogai et al. | 252/299.67 |
| 4,589,996 | 5/1986 | Inoue et al. | 252/299.65 |
| 4,596,667 | 6/1986 | Inukai et al. | 252/299.63 |
| 4,613,209 | 9/1986 | Goodby et al. | 252/299.6 |
| 4,614,609 | 9/1986 | Inoue et al. | 252/299.66 |
| 4,615,586 | 10/1986 | Geary et al. | 350/350 S |
| 4,617,140 | 10/1986 | Eidenschink et al. | 252/299.63 |
| 4,622,165 | 11/1986 | Kamo et al. | 252/299.01 |
| 4,647,398 | 3/1987 | Saito et al. | 252/299.67 |
| 4,659,651 | 9/1987 | Higuchi et al. | 252/299.66 |

FOREIGN PATENT DOCUMENTS

| | | | |
|---|---|---|---|
| 87032 | 4/1985 | European Pat. Off. | 252/299.61 |
| 136725 | 4/1985 | European Pat. Off. | 252/299.01 |
| 174816 | 3/1986 | European Pat. Off. | 252/299.67 |
| 188222 | 7/1986 | European Pat. Off. | 252/299.65 |
| 191600 | 8/1986 | European Pat. Off. | 252/299.67 |
| 192267 | 8/1986 | European Pat. Off. | 252/299.61 |
| 194659 | 9/1986 | European Pat. Off. | 252/299.01 |
| 3515373 | 11/1986 | Fed. Rep. of Germany | 252/299.61 |
| 3534777 | 4/1987 | Fed. Rep. of Germany | 252/299.67 |
| 58-29877 | 2/1983 | Japan | 252/299.60 |
| 58-46040 | 3/1983 | Japan | 252/299.66 |
| 59-157056 | 9/1984 | Japan | 252/299.63 |
| 61-68449 | 4/1986 | Japan | 252/299.66 |
| 8600087 | 1/1986 | PCT Int'l Appl. | 252/299.61 |
| 8606373 | 11/1986 | PCT Int'l Appl. | 252/299.61 |

OTHER PUBLICATIONS

Gerber, P. R., Mol. Cryst. Liq. Cryst., vol. 124 (1–4), pp. 163–177 (1985).

(List continued on next page.)

[57] ABSTRACT

Novel compounds for use in ferroelectric smectic liquid crystal mixtures are provided, having a general formula:

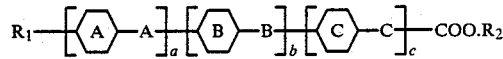

where $R_1$ is alkyl, alkoxy, alkylcarbonyloxy or alkoxycarbonyl,

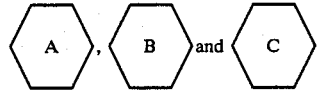

are cyclic groups, A and B are a single bond, COO, OOc, $CH_2CH_2$, $CH_2O$ or $OCH_2$, (a+b+c) is 2 or 3 and $R_2$ is an optically active alkyl group. Ferroelectric smectic liquid crystal mixtures containing these compounds, and a suitable ferroelectric liquid crystal device are also described.

5 Claims, 1 Drawing Sheet

OTHER PUBLICATIONS

Gerber, P. R., Mol. Cryst. Liq. Cryst., vol. 116 (3-4), pp. 197-206 (1985).

C.A. 94: 208491, (1981).

Gray, G. E. et al., Mol. Cryst. Liq. Cryst., vol. 37, pp. 157-188 (1976).

Goodby, J. W., et al., Liquid Crystals and Ordered Fluids, vol. 4, Griffin, A., et al. Ed., Plenum Press, N.Y., pp. 1-32 (1985).

Gray, G. W., et al., Liquid Crystals & Plastic Crystals, vol. 1, pp. 142-143, Ellis Horwood, Ltd., London (1974).

Chemical Abstracts, vol. 99, No. 19, Nov. 17, 1983, p. 580, Abstract No. 158024q, Columbus, Oh., U.S.; & JP-A-58 46 040 (CHISSO Corp) 17-03-1983.

*Primary Examiner*—Teddy S. Gron
*Attorney, Agent, or Firm*—Stevens, Davis, Miller & Mosher

SECONDARY ALCOHOL DERIVATIVES FOR USE IN LIQUID CRYSTAL MATERIALS AND DEVICES

This invention relates to liquid crystal mixtures and to compounds derived from optically active secondary alcohols for use in them. The invention is particularly concerned with ferroelectric smectic liquid crystal mixtures and compounds. The invention also relates to electro-optical devices incorporating these mixtures.

Ferroelectric smectic liquid crystal materials utilise the ferroelectric properties of the chiral tilted smectic phase, ie the chiral smectic C, F, G, H, I, F and K phase (hereinafter designated $S_c^*$ etc, the asterisk * denoting chirality). The $S_c^*$ phase is most commonly sought for use in electro-optical devices as it is the most fluid, and it is also desirable that the material shows an $S_A$ phase and a nematic (N) phase at temperatures above the $S_c^*$ phase, to assist in surface alignment.

Ferroelectric liquid crystal materials ideally have a low viscosity, a broad smectic liquid crystal temperature range, stability etc, and in particular should show a high spontaneous polarisation coefficient (Ps, measured in $nCcm^{-2}$). Although some single component materials show these properties, it has become common practice to use a two-component mixture (wherein each component may itself be a mixture of compounds) in which one component is a tilted smectic material without necessarily being chiral, termed a 'host' and the other component is chiral without necessarily showing a smectic phase (although it is preferred if it does), termed a 'dopant'. The mixing of the dopant with the host produces a chiral tilted smectic mixture, ideally also inducing a high Ps. In some circumstances the host need not show a tilted smectic phase until it is mixed with the dopant, but this is less common.

The general structure of liquid crystalline compounds is well known. There is normally a mesogenic (in this case smectogenic) 'core' consisting of a linear chain of cyclic groups such as phenyl or cyclohexyl linked either directly or indirectly, with various terminal or lateral substituents one of which must be optically active to induce a chiral liquid crystal phse. Within this generalised picture there is almost endless scope for variation to identify useful liquid crystal compounds, as seemingly minor structural changes can have drastic effects upon the liquid crystal properties. This is especially so in the case of ferroelectric smectic mixtures where the ground rules for miscibility and effective host-dopant interaction are still under investigation.

This is a field in which small changes in molecular architecture can have drastic effects upon the liquid crystal characteristics of a compound, for example as discussed in Gray and Goodby, Mol Cryst Liq Cryst (1976) 37 157-188, with reference to smectic liquid crystal compounds which are esters, for example of structure:

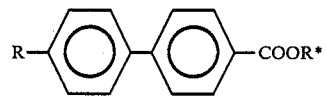

where R is n-alkoxy and R* is a 1-methyl alkyl group.

European Patent Application No. 0110299 discloses a series of compounds many of which show smectic liquid crystal phases, but which contain only phenyl groups in the molecular core. This EPA also discloses ferroelectric smectic liquid crystal materials which are mixtures containing one or more of the smectic members of this series, for example esters of the formula

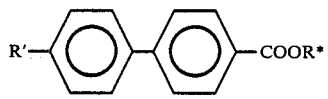

where R' is an alkyl group and R* is optically active 2-methylheptyl (2-octyl) or 2-methylbutyl.

It is an object of the present invention to provide more novel compounds which may be used as chiral dopants in ferroelectric smectic liquid crystal mixtures, and also to provide novel mixtures containing them. Further objects and advantages of the invention will be apparent from the following description.

According to the present invention there is provided a novel optically active ester of Formula I below:

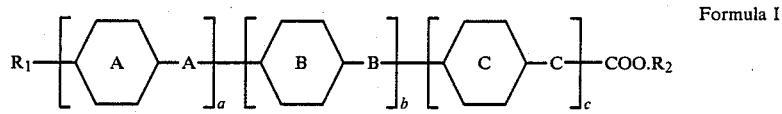

Formula I wherein $R_1$ is selected from hydrogen or C1–15 alkyl, alkoxy, alkylcarbonyloxy and alkoxycarbonyl wherein each of the cyclic groups

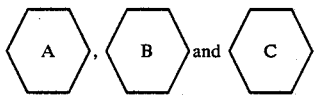

is independently selected from optionally substituted phenyl, pyridyl, pyrimidyl, trans-cyclohexyl, dioxane, piperidyl and bicyclo (2,2,2) octyl provided that if $R_1$ is alkyl or alkoxy, then

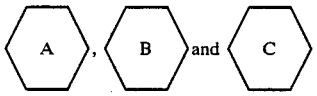

are not all phenyl,
wherein each of A and B is independently selected from COO, OOC, $CH_2CH_2$, $CH_2O$, $OCH_2$ or a single bond,
wherein each of a b, and c is independently 0 or 1 provided that (a+b+c) is 2 or 3,
and wherein $R_2$ is an optically active alkyl group of structure $-C^*H(C_mH_{2m+1})C_nH_{2n+1}$ where m is an integer in the range 1–5 and n is an integer in the range 1 to 20 provided that m is not equal to n.

Many of the new compounds of Formula I are useful dopants, as defined above, in ferroelectric smectic liquid crystal mixtures. Accordingly the invention also provides a novel ferroelectric smectic liquid crystal mixture which contains at least one compound of Formula I.

The relative usefulness of the compounds of Formula I as dopants, eg their smectic, particularly $S_c^*$, character, the Ps they induce and other desired properties that are manifest in ferroelectric smectic liquid crystal mixtures which contain them are among the factors determining the structural preferences discussed below.

Preferably $R_1$ is or contains a straight chain $C_6$–$C_{10}$ alkyl or alkoxy group, eg $R_1$ may be hexyl, heptyl, octyl, nonyl or decyl or the corresponding alkoxy group. Alternatively, and equally preferred, $R_1$ may be or contain an optically active alkyl group $R^*$ of structure

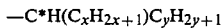

where y is an integer in the range 1–5 and x is an integer in the range 1 to 20 provided that x is not equal to y. In this case y is preferably 1 and x is 1 to 10, particularly y=1 and x is 5, 6 or 7. When $R_1$ contains such an optically active alkyl group, $R_1$ is preferably an alkoxycarbonyl group, ie $R^*OOC-$ where $R^*$ is the optically active alkyl group.

The compound of Formula I preferably contains no more than two of the groups

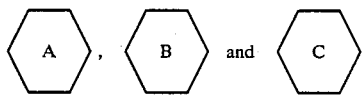

Preferably these cyclic groups are selected from phenyl, pyrimidyl and cyclohexyl, and are unsubstituted by lateral substituents. When these cyclic groups do carry lateral substituents they may be selected from methyl, $CF_3$, CN, F, Cl or Br. Fluorine is a preferred substituent. When lateral substituents are present on the group

they are preferably in one or both of the positions adjacent to the —COO— link.

The links A and B are preferably either single bonds or ester groups. Some particularly preferred structural forms for the compound of Formula I are listed in Table 1 below.

TABLE 1

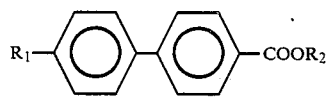

TABLE 1-continued

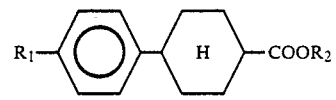

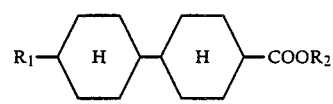

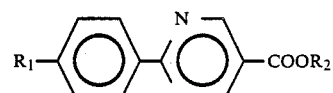

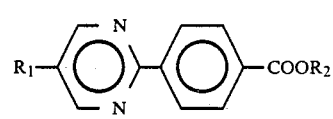

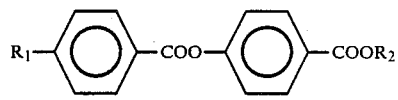

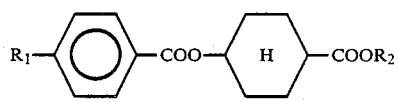

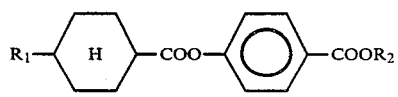

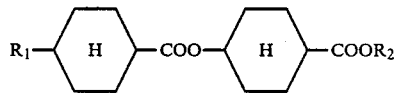

Where

represents trans cyclohexyl.

The optically active alkyl group $R_2$ preferably has m=1 and n-1 to 10, particularly m=1 and n=5, 6 or 7 ie 1-methylhexyl, 1-methylheptyl or 1-methyloctyl.

Many of the compounds of Formula I are useful dopants in ferroelectric smectic liquid crystal mixtures and induce a high Ps in a mixture with a host. The inducement of increase Ps in a tilted chiral smectic material by addition of a compound of Formula 1 is generally most marked at lower temperatures and decreases as the mixture approaches a phase transition to a non-tilted chiral smectic phase for example on Sc to SA transition.

For use as a chiral dopant in a ferroelectric smectic liquid crystal mixture, the compound of Formula I may have a chiral centre of either S or R configuration which may confer either (+) or (−) senses of optical rotation on the molecule (configurations and senses of optical rotation need not correspond). When the compound of Formula I contains two chiral centres, ie $R_1$ is one of the optically active groups referred to above then the configurations of the chiral centres and their senses of optical rotation may be the same or different.

It is preferred that the sense of Ps induced in a mixture by each chiral centre, if two are present in the molecule, is the same so that a high Ps is induced. Advantageously the two chiral centres may induce opposing senses of helical twist in the chiral smectic phase, but the same sense of Ps, so that a material with a long, preferably infinite pitch may be obtained, with a high Ps.

Compounds of Formula I may be used as chiral dopants in a wide variety of tilted smectic hosts. Some examples of suitable known hosts are the compounds listed in Table 2 below, or mixtures of them. A particularly preferred series of compounds for use as or in a tilted smectic host is the series of esters descrbed in copending patent application PCT/GB86/0040, the contents of which are included herein by reference. These esters have the general formula

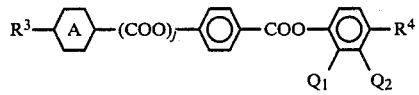

Formula II where

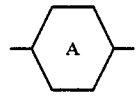

repesents 1,4-phenyl or trans-1,4-cyclohexyl, $R^3$ represents $C_{3-12}$ alkyl, alkoxy, alkylcarbonyloxy, alkoxy-carbonyl, or alkoxycarbonyloxy, j is 0 or 1, $R^4$ represents $C_{3-12}$ alkyl or alkoxy, one of $Q_1$ or $Q_2$ is H and the other F. Especially preferred esters of Formula II for use in or as a host together with a compound of Formula I as dopant are those below, where $R^5$ is alkyl or alkoxy:

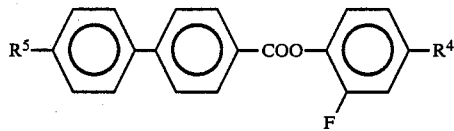

and

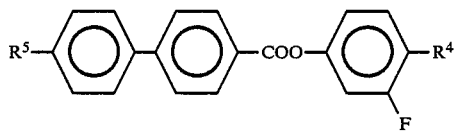

TABLE 2

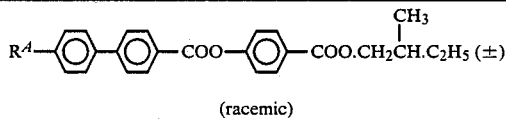

(racemic)

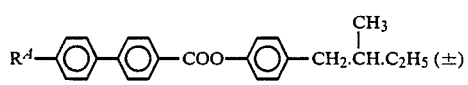

TABLE 2-continued (racemic)

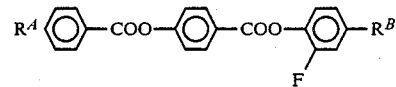

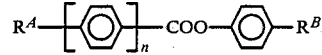

Where $R^A$ and $R^B$ may be $C_1$-$C_{12}$ n-alkyl or n-alkoxy, e.g $R^A = C_8H_{17}$ or $C_8H_{17}O$ and $R^B = C_5H_{11}$, and n is 1 or 2.

TABLE 3

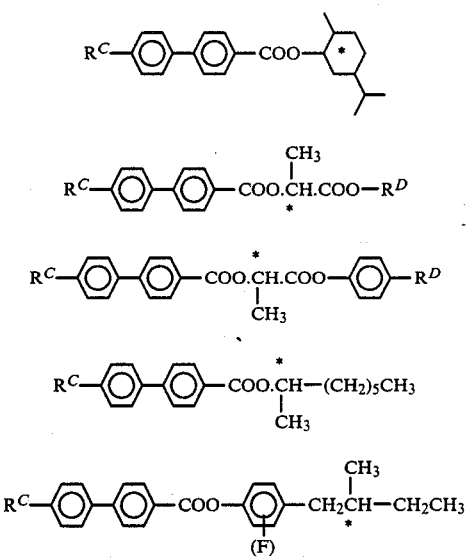

Where $R^C$ may be n-alkyl or n-alkoxy, and $R^D$ may be n-alkyl, or n-alkoxy if not present as —COOR$^D$. $R^C$ and $R^D$ may independently contain 1–12 carbon atoms.

Ferroelectric smectic liquid crystal mixtures containing a compound of Formula I may also contain other chiral dopants, and such other dopants may induce the same or the opposite sense of helical pitch on the chiral smectic phase of the mixture. If the latter, then a mixture may be obtained in some cases which has an infinite pitch, and if the senses of Ps induced by the compound of Formula I and the dopant(s) are additive, ie the same, then the mixture may also have a large Ps. Some examples of other known types of dopant which can be used in this way with a compound of Formula I are listed in Table 3 above.

In addition to a compound of Formula I, a host material, and any other chiral dopants which may be present, a ferroelectric smectic liquid crystal material may also contain other known additives to modify or improve its properties if this is considered necessary, such as viscosity, liquid crystal transition temperatures, birefringence, etc.

A typical ferroelectric smectic liquid crystal mixture which incorporates a compound of Formula I has the following composition:

| | |
|---|---|
| Host, eg Table 2 compound, ester of | up to 99 wt % |

| | |
|---|---|
| Formula II, or mixtures thereof. One or more compounds of Formula I | up to 50 wt % (preferably 1 to 30 wt %) |
| Other dopant, eg Table 3 compound | up to 30 wt % |
| Additives to modify properties | up to 30 wt % |
| The total being 100 % | |

The actual composition selected will depend upon the properties required. Ps is generally proportional to the amount of chiral dopants present in the mixture, and it is desirable to achieve as high a Ps as possible without compromise of other desirable properties.

Ferroelectric smectic liquid crystal materials incorporating a compound of Formula I may be used in any of the known types of electro optic device which use such materials, for example as generally described in Appl. Phys. Lett. 36, (1980) p 899. (Reference 1).

An example of such a device is the "Clark Lagerwall Device", described in Reference 1, and also in "Recent Developments in Condensed Matter Physics" 4, p309, (1981) (Reference 2). The physics of this device, and methods of constructing one are well known. In practice such a device usually consists of two substrates, at least one of which is optically transparent, electrodes on the inner surfaces of the substrates and a layer of the liquid crystal material sandwiched between the substrates.

The Clark Lagerwall device uses a layer of liquid crystal material between the substrates of a thickness comparable to or less than the helical pitch of the S* configuration, which causes the helix to be unwound by surface interactions. In its unwound state the material has two surface stabilised states with director orientations (ie molecular tilt direction) at twice the tilt angle to one another, and also permanent dipole orientations perpendicular to the substrates but in opposite directions.

An alternative approach to providing cells for a Clark-Lagerwall device having a thicker layer of liquid crystal material is to use an applied electric field to induce homogeneous alignment through interaction with the dielectric anistropy of the liquid crystal material. This effect requires a chiral smectic material having a negative dielectric anisotropy, eg provided by incorporation of a compound having a lateral halogen or cyano substituent. Such a compound may itself be chiral or non-chiral and smectic or non-smectic.

In general chiral smectic C materials ($S_C^*$) are used in these displays because these are the most fluid, but in principle the more ordered chiral smectics could also be used. A pleochroic dye may also be incorporated in the liquid crystal material to enhance the electro-optic effect.

Such a device incorporating compounds of Formula I offers the possibility of a high switching speed of a few microseconds—as demonstrated in Reference 2—together with bistable storage capability; consequently it is likely to have important applications in displays, optical processing devices, and optical storage devices.

According to a further aspect of the invention, there is provided an electro-optical device, operating by a ferroelectric effect in a liquid crystal material, wherein the liquid crystal material is a mixture of compounds at least one of which is a compound of formula I. The liquid crystal material may be one of those discussed above.

The device may for example be a Clark-Lagerwall device as described above, and may comprise two substrates, at least one of which is optically transparent, electrodes on the inner surfaces of the substrates, and a layer of the liquid crystal material sandwiched between the substrates.

The ferroelectric liquid crystal materials of the invention are especially suitable for use in rapidly switched large screen displays, eg portable computers, desk top calculators and visual display units, and by using appropriately shaped substrates and electrodes the device of the invention may be made in this form.

Compounds of Formula I are esters and as such may be prepared by well known esterification methods, most conveniently from the appropriate carboxylic acid and the optically active alcohol $R_2^*OH$. The carboxylic acids are in many cases commercially available or may be prepared by routes which will be apparent to the skilled chemist, eg by hydrolysis of a commercially available cyanide. Many of the alcohols $R_2^*OH$ are commercially available in an optically pure form, eg 1-methylheptanol (2-octanol) in its S-(+)- or R-(−)- enantiomers.

Various esterification methods will be apparent to the skilled chemist, or may be found in the chemical literature, for example the sulphuric acid and acid chloride methods described in Gray and Goodby (op cit).

The invention will now be described by way of example with reference to the accompanying drawing which shows a cross sectional view of an electro-optical liquid crystal device suitable for use with the liquid crystal mixtures of the invention.

Preparation of S-(+)- or R-(−)-2-octyl carboxylic acid esters

A solution of S-(+)-2-octanol (17.6 g, 0.135 mol) in pyridine (70 ml) was added to a solution of the appropriate carboxylic acid chloride (0.05 mol) in toluene (70 ml) over 10 minuts and the mixture was stirred and heated at 90° C. for 3 hours. The cooled reaction mixture was acidified with 6N hydrochloric acid and the organic layer washed with water (100 ml), 2N sodium hydroxide solution (100 ml) and saturated sodium chloride solution (100 ml). It was then crude dried over sodium sulphate and evaporated to dryness. The cooled product was crystallised twice from ethanol containing a drop of pyridine, and the resulting slightly coloured ester dissolved in a 2:1 mixutre of petroleum ether (60°–80°) and dichloromethane and passed through a column of alumina (926 g). Evaporation gave a pure ester. The optical enantiomer was prepared in the same way from R-(−)-2-octanol.

Chlorides of the carboxylic acids listed below were used to produce esters in this way:

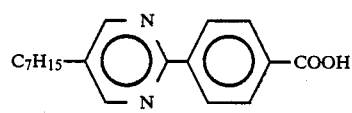

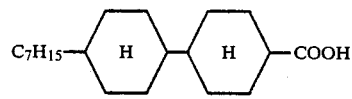

-continued

The properties of the resulting esters in ferroelectric smectic liquid crystal mixtures were examined by measurement of the important property Ps. In all the measurements listed below the host was a 50:50 by weight mixture of the two compounds:

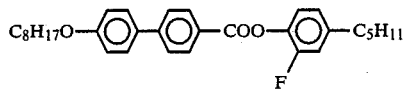

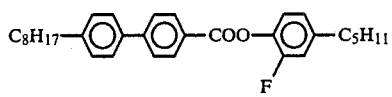

which are compounds of Formula II referred to above.

The results are listed below as tables showing the variation of the spontaneous polarisation coefficient Ps (in nC cm$^{-2}$) with temperature (T, in °C.).

(Note: Oct represents optically active 2-octyl. Examples 1 and 2 were measured at 10 wt % concentration in the host example 3 at 5 wt %).

EXAMPLE 1

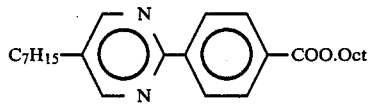

| T | Ps |
| --- | --- |
| 0 | 5.5 |
| 10 | 5.1 |
| 20 | 3.9 |
| 30 | 2.9 |
| 35 | 1.9 |
| 40 | 0.1 |

EXAMPLE 2

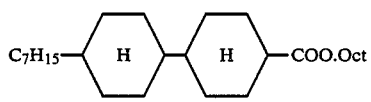

| T | Ps |
| --- | --- |
| 21.3 | 1.7 |
| 25 | 1.3 |
| 28 | 0.4 |
| 30 | 0.1 |

EXAMPLE 3

| T | Ps |
| --- | --- |
| 24.5 | 5.7 |
| 30 | 5.6 |
| 40 | 4.9 |
| 50 | 4.0 |
| 60 | 3.1 |
| 70 | 2.2 |
| 75 | 1.6 |
| 80 | 1.1 |
| 85 | 0.5 |

Examples 1, 2 and 3 above demonstrate that compounds of Formula I may be used as dopants in ferroelectric smectic liquid crystal mixtures.

An example of the use of a compound of Formula I in a liquid crystal device embodying the present invention will now be described with reference to the accompanying drawing which is a cross-sectional end view of a liquid crystal shutter.

A liquid crystal cell comprises a layer 1 of liquid crystal material exhibiting a chiral smectic phase sandwiched between a glass slide 2 having a transparent conducting layer 3 on its surface, eg of tin oxide or indium oxide, and a glass slide 4 having a transparent conducting layer 5 on its surface. The slides 2,4 bearing the layers 3,5 are repectively coated by films 6,7 of a polyimide polymer. Prior to construction of the cell the films 6 and 7 are rubbed with soft tissue in a given direction, the rubbing direction being arranged parallel upon construction of the cell. A spacer 8, eg of mylar, separates the slides 2,3 to the required distance, eg 5 microns. The liquid crystal material 1 is introduced between the slides 2,3 to the required distance, eg 5 microns. The liquid crystal material 1 is introduced between the slide 2,3 by filling the space between the slides 2,3 and spacer 8 and sealing the spacer 8 in a vacuum in a known way.

A polarizer 9 is arranged with its polarization axis parallel to the rubbing direction on the films 6,7 and an analyzer (crossed polarizer) 10 is arranged with its polarization axis perpendicular to that rubbing direction.

When a square wave voltage (from a conventional source not shown) varying between about +10 volts and −10 volts is applied across the cell by making contact with the layers 4 and 5 the cell is rapidly switched upon the change in sign of the voltage between a dark state and a light state as explained above.

We claim:

1. A ferroelectric smectic liquid crystal material characterized in that it is a mixture of at least two compounds, at least one of which is a compound of formula:

where R* is an optically active alkyl group of structure

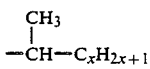

where x is in the range 2 to 10, and $R^*_2$ is an optically active alkyl group of structure

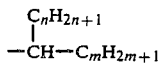

where m is an integer in the range 1 to 5 and n is an integer in the range 1 to 20 provided that m is not equal to n.

2. A ferroelectric smectic liquid crystal material according to claim 1, characterized in that $R^*$ and $R^*_2$ are both —$CH(CH_3)C_6H_{13}$.

3. A ferroelectric smectic liquid crystal material according to claim 1 or claim 2, characerized in that it contains in addition one or more compounds of a formula selected from the class consisting of

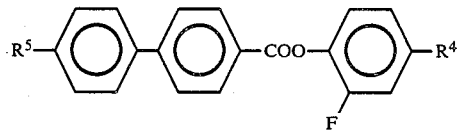

and

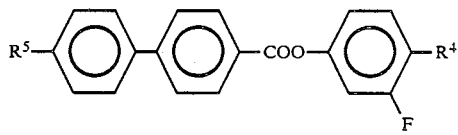

where $R^4$ and $R^5$ represent alkyl or alkoxy containing 3 to 12 carbon atoms.

4. A ferroelectric smectic liquid crystal material according to claim 3, characterized in that it contains a mixture of the two compounds

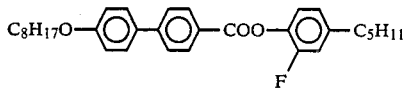

and

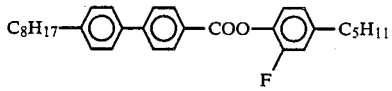

5. An electro-optical device, operating by a ferroelectric effect in a liquid crystal material, characterized in that the liquid crystal material is a material as claimed in claim 1.

* * * * *